(12) United States Patent
Asano et al.

(10) Patent No.: US 8,903,044 B2
(45) Date of Patent: Dec. 2, 2014

(54) X-RAY DIFFRACTION APPARATUS

(75) Inventors: Sigematsu Asano, Tokyo (JP); Ichiro Tobita, Tokyo (JP); Atsushi Ohbuchi, Tokyo (JP); Takayuki Konya, Tokyo (JP)

(73) Assignee: Rigaku Corporation, Tokyo (JP)

( * ) Notice: Subject to any disclaimer, the term of this patent is extended or adjusted under 35 U.S.C. 154(b) by 299 days.

(21) Appl. No.: 13/361,505

(22) Filed: Jan. 30, 2012

(65) Prior Publication Data

US 2012/0195406 A1 Aug. 2, 2012

(30) Foreign Application Priority Data

Jan. 31, 2011 (JP) ................................. 2011-017511

(51) Int. Cl.
*G01N 23/20* (2006.01)
*G01N 23/207* (2006.01)

(52) U.S. Cl.
CPC ........ *G01N 23/20008* (2013.01); *G01N 23/207* (2013.01); *G01N 2223/32* (2013.01); *G01N 2223/316* (2013.01)
USPC .............................................. 378/81; 378/71

(58) Field of Classification Search
CPC ............ G01N 23/20; G01N 23/20008; G01N 23/20016; G01N 23/207; G01N 2223/316; G01N 2223/32
USPC .......................................... 378/71, 81, 73, 79
See application file for complete search history.

(56) References Cited

U.S. PATENT DOCUMENTS

| 2006/0023838 A1* | 2/2006 | He et al. .......................... 378/81 |
| 2006/0062350 A1 | 3/2006 | Yokhin et al. |
| 2006/0062351 A1 | 3/2006 | Yokhin et al. |
| 2011/0164730 A1* | 7/2011 | Yokhin et al. ................... 378/73 |

FOREIGN PATENT DOCUMENTS

| JP | 8-262196 A | 10/1996 |
| JP | 10-48398 A | 2/1998 |
| JP | 2000-206059 A | 7/2000 |
| JP | 2001-83105 A | 3/2001 |
| JP | 2006-138837 A | 6/2006 |

OTHER PUBLICATIONS

Wikipedia, "Cam", (Feb. 15, 2010), Retrieved from the Internet <URL: http://web.archive.org/web/20100215125822/http://en.wikipedia.org/wiki/Cam>.*
Office Action dated Sep. 17, 2014, issued in corresponding Japanese Patent Application No. 2012-018618 (3 pages).

* cited by examiner

*Primary Examiner* — Glen Kao
(74) *Attorney, Agent, or Firm* — Westerman, Hattori, Daniels & Adrian, LLP

(57) ABSTRACT

An X-ray shielding member is provided so as to confront an X-ray incident face of a sample, and a gap through which an X-ray emitted from an X-ray source is passed and irradiated to an X-ray incident face of the sample is formed between the X-ray shielding member and the X-ray incident face of the sample. A gap adjusting mechanism for moving the X-ray shielding member is further provided to move the X-ray shielding member in accordance with change of an X-ray incident angle to the sample by a goniometer, whereby the breadth of the gap formed between the X-ray shielding member and the X-ray incident face of the sample can be adjusted.

6 Claims, 17 Drawing Sheets

Fig. 7

| 2θ (deg.) | θ (deg.) | a(mm) | b(mm) | c(mm) | c+L/2 | θx (deg.) | H(mm) | L(mm) |
|---|---|---|---|---|---|---|---|---|
| 90 | 45 | 150 | 106.07 | 106.07 | 116.07 | 42.42 | 9.14 | 20 |
| 80 | 40 | 150 | 96.42 | 114.91 | 124.91 | 37.67 | 7.72 | 20 |
| 70 | 35 | 150 | 86.04 | 122.87 | 132.87 | 32.92 | 6.48 | 20 |
| 60 | 30 | 150 | 75.00 | 129.90 | 139.90 | 28.19 | 5.36 | 20 |
| 50 | 25 | 150 | 63.39 | 135.95 | 145.95 | 23.48 | 4.34 | 20 |
| 40 | 20 | 150 | 51.30 | 140.95 | 150.95 | 18.77 | 3.40 | 20 |
| 30 | 15 | 150 | 38.82 | 144.89 | 154.89 | 14.07 | 2.51 | 20 |
| 20 | 10 | 150 | 26.05 | 147.72 | 157.72 | 9.38 | 1.65 | 20 |
| 10 | 5 | 150 | 13.07 | 149.43 | 159.43 | 4.69 | 0.82 | 20 |
| 4 | 2 | 150 | 5.23 | 149.91 | 159.91 | 1.88 | 0.33 | 20 |
| 2 | 1 | 150 | 2.62 | 149.98 | 159.98 | 0.94 | 0.16 | 20 |

Fig. 12

| 2θ (deg.) | θ (deg.) | a(mm) | b(mm) | c(mm) | θx (deg.) | c+L/2 | L/2(mm) | H(mm) | L (mm) | β (deg.) |
|---|---|---|---|---|---|---|---|---|---|---|
| 90 | 45 | 150 | 106.07 | 106.07 | 44.5 | 107.93 | 1.87 | 1.84 | 3.74 | 1 |
| 80 | 40 | 150 | 96.42 | 114.91 | 39.5 | 116.96 | 2.06 | 1.70 | 4.12 | 1 |
| 70 | 35 | 150 | 86.04 | 122.87 | 34.5 | 125.18 | 2.31 | 1.59 | 4.62 | 1 |
| 60 | 30 | 150 | 75.00 | 129.90 | 29.5 | 132.56 | 2.66 | 1.50 | 5.32 | 1 |
| 50 | 25 | 150 | 63.39 | 135.95 | 24.5 | 139.10 | 3.16 | 1.44 | 6.31 | 1 |
| 40 | 20 | 150 | 51.30 | 140.95 | 19.5 | 144.88 | 3.92 | 1.39 | 7.84 | 1 |
| 30 | 15 | 150 | 38.82 | 144.89 | 14.5 | 150.12 | 5.23 | 1.35 | 10.46 | 1 |
| 20 | 10 | 150 | 26.05 | 147.72 | 9.5 | 155.65 | 7.93 | 1.33 | 15.86 | 1 |
| 10 | 5 | 150 | 13.07 | 149.43 | 4.5 | 166.11 | 16.68 | 1.31 | 33.37 | 1 |
| 4 | 2 | 150 | 5.23 | 149.91 | 1.5 | 199.91 | 50.01 | 1.31 | 100.01 | 1 |
| 2 | 1 | 150 | 2.62 | 149.98 | 0.5 | 299.98 | 150.00 | 1.31 | 300.00 | 1 |

Fig.16

| 2θ (deg.) | θ (deg.) | a(mm) | b(mm) | c(mm) | d(mm) | e(mm) | e+L/2(mm) | H(mm) | L/2(mm) | W/2(mm) |
|---|---|---|---|---|---|---|---|---|---|---|
| 90 | 45 | 150 | 106.07 | 106.07 | 110.59 | 101.54 | 111.54 | 9.91 | 10 | 6.4 |
| 80 | 40 | 150 | 96.42 | 114.91 | 101.32 | 110.79 | 120.79 | 8.39 | 10 | 6.4 |
| 70 | 35 | 150 | 86.04 | 122.87 | 91.28 | 119.20 | 129.20 | 7.07 | 10 | 6.4 |
| 60 | 30 | 150 | 75.00 | 129.90 | 80.54 | 126.70 | 136.70 | 5.89 | 10 | 6.4 |
| 50 | 25 | 150 | 63.39 | 135.95 | 69.19 | 133.24 | 143.24 | 4.83 | 10 | 6.4 |
| 40 | 20 | 150 | 51.30 | 140.95 | 57.32 | 138.76 | 148.76 | 3.85 | 10 | 6.4 |
| 30 | 15 | 150 | 38.82 | 144.89 | 45.00 | 143.23 | 153.23 | 2.94 | 10 | 6.4 |
| 20 | 10 | 150 | 26.05 | 147.72 | 32.35 | 146.61 | 156.61 | 2.07 | 10 | 6.4 |
| 10 | 5 | 150 | 13.07 | 149.43 | 19.45 | 148.87 | 158.87 | 1.22 | 10 | 6.4 |
| 5 | 2.5 | 150 | 6.54 | 149.86 | 12.94 | 149.58 | 159.58 | 0.81 | 10 | 6.4 |

Fig.17

| 2θ (deg.) | θ (deg.) | a(mm) | b(mm) | c(mm) | d(mm) | e(mm) | e+L/2(mm) | H(mm) | L/2(mm) | W/2(mm) | β (deg.) |
|---|---|---|---|---|---|---|---|---|---|---|---|
| 90 | 45 | 150 | 106.07 | 106.07 | 110.59 | 101.54 | 103.38 | 1.97 | 1.84 | 6.4 | 1 |
| 80 | 40 | 150 | 96.42 | 114.91 | 101.32 | 110.79 | 112.81 | 1.81 | 2.02 | 6.4 | 1 |
| 70 | 35 | 150 | 86.04 | 122.87 | 91.28 | 119.20 | 121.45 | 1.69 | 2.25 | 6.4 | 1 |
| 60 | 30 | 150 | 75.00 | 129.90 | 80.54 | 126.70 | 129.28 | 1.61 | 2.58 | 6.4 | 1 |
| 50 | 25 | 150 | 63.39 | 135.95 | 69.19 | 133.24 | 136.28 | 1.54 | 3.04 | 6.4 | 1 |
| 40 | 20 | 150 | 51.30 | 140.95 | 57.32 | 138.76 | 142.50 | 1.50 | 3.74 | 6.4 | 1 |
| 30 | 15 | 150 | 38.82 | 144.89 | 45.00 | 143.23 | 148.13 | 1.49 | 4.90 | 6.4 | 1 |
| 20 | 10 | 150 | 26.05 | 147.72 | 32.35 | 146.61 | 153.79 | 1.51 | 7.18 | 6.4 | 1 |
| 10 | 5 | 150 | 13.07 | 149.43 | 19.45 | 148.87 | 162.53 | 1.63 | 13.66 | 6.4 | 1 |
| 5 | 2.5 | 150 | 6.54 | 149.86 | 12.94 | 149.58 | 174.59 | 1.85 | 25.01 | 6.4 | 1 |

X-RAY DIFFRACTION APPARATUS

BACKGROUND OF THE INVENTION

1. Field of the Invention

The present invention relates to an X-ray diffraction apparatus for detecting a diffraction X-ray diffracted from a sample by an X-ray detector when the sample is irradiated with an X-ray.

2. Description of Related Art

According to a general X-ray diffraction apparatus, a sample is irradiated with an X-ray emitted from an X-ray source while divergence of the X-ray is limited to a predetermined angle range by a divergence limiting slit (divergence slit). Diffraction of the X-ray occurs in the sample and thus a diffraction X-ray occurs from the sample when a Bragg's diffraction condition is satisfied between the X-ray irradiated to the sample and crystal lattice planes of the sample. The diffraction X-ray emitted from the sample is detected by an X-ray detector.

In the normal X-ray diffraction apparatus, scattered X-rays occur when an X-ray emitted from an X-ray source impinges against a divergence limiting slit. The scattered X-rays cause background noise for the diffraction X-ray from the sample as a measurement target, and thus the scattered X-rays must be prevented from being incident to the X-ray detector as much as possible.

The factor causing the scattered X-rays is not limited to the divergence limiting slit. When some member exists on an X-ray optical path between the X-ray source and the sample, scattered X-rays may occur from the member.

When a detector configured to detect a diffraction X-ray in a narrow range such as a scintillation counter or the like is used as an X-ray detector, it is normal to dispose a receiving slit and an anti scatter slit (scattering slit). Scattered X-rays occurring at the divergence limiting slit are prevented from traveling by the receiving slit and the anti scatter slit to significant degree.

However, when one-dimensional X-ray detectors such as photosensor arrays or position sensitive type detectors such as PSPC (Position Sensitive Proportional Counter) or the like are arranged in a scan direction and used as an X-ray detector or when a two-dimensional X-ray detector such a CCD, a pixel detector or the like which detects a diffraction X-ray in a planarly broad range is used, it is impossible to dispose the receiving slit, the anti scatter slit or the like in front of the X-ray detector, so that scattered X-rays occurring at the divergence limiting slit are directly incident into the X-ray detector and detected by the X-ray detector. As a result, there may occur a problem that the background of measurement data increases and thus the measurement precision is reduced or scattered X-rays are erroneously detected as a peak value.

In order to overcome the background increasing problem caused by the scattered X-rays as described above, according to an X-ray diffraction apparatus disclosed in Patent Document 1 (JP-A-10-48398), an X-ray shielding member is disposed so as to confront a sample through a gap (interval) through which an incident X-ray passes. According to this X-ray diffraction apparatus, even when some member, for example, a divergence limiting slit is disposed on an X-ray optical path between an X-ray source and the sample and thus scattered X-rays or the like occur at the member concerned, traveling of the scattered X-rays or the like to an X-ray detector is obstructed by the action of the X-ray shielding member which is disposed so as to confront the sample, whereby the scattered X-rays or the like can be prevented from being taken into the X-ray detector.

Furthermore, an X-ray diffraction apparatus disclosed in Patent Document 2 (JP-A-2001-83105) is provided with not only a shielding body for shielding scattered X-rays, but also a shielding body moving mechanism for moving the shielding body to a specified position. The shielding body moving mechanism contains a Z stage which is fixed onto a surface plate independently of a goniometer, and an XY translation stage disposed on the Z stage. After the position of the shielding body is adjusted, the shielding body moving mechanism is kept at a fixed position irrespective of movement and rotation of the sample. Specifically, the shielding body can be moved in the vertical direction by the Z stage of the shielding body moving mechanism, and the movement of the shielding body is adjusted so that the center of the shielding body is coincident with the height of a primary X-ray beam (incident X-ray). Furthermore, the shielding body can be moved within a horizontal plane by the XY translation stage.

In the conventional X-ray diffraction apparatuses disclosed in the respective patent documents, each of the X-ray shielding member and the shielding body is fixed to keep a fixed relative position with respect to the sample during execution of an X-ray diffraction measurement, so that the gap through which the incident X-ray is passed is kept to be fixed.

It is originally preferable that the gap formed between the sample and the X-ray shielding member or the shielding body is adjusted in conformity with the width of an incident X-ray which is emitted from the X-ray source and whose divergence angle is limited to a predetermined angle range by the divergence limiting slit, thereby setting the breadth of the gap so that the whole incident X-ray is passed through the gap and only scattered X-rays appearing around the incident X-ray are obstructed.

When the incident angle θ of the X-ray to the sample is changed by so-called θ-2θ scan which is executed in the X-ray diffraction measurement, the width of the incident X-ray varies in connection with the change of the incident angle θ at the confronting position where the X-ray shielding member or the shielding body is disposed so as to confront the sample. Therefore, in the conventional X-ray diffraction apparatus in which the gap formed between the sample and the X-ray shielding member or the shielding body is kept fixed, the gap concerned may be smaller than the width of the incident X-ray, so that traveling of the incident X-ray is obstructed by the X-ray shielding member or the shielding body. Or, conversely, the gap concerned may be larger than the width of the incident X-ray, so that a part of scattered X-rays is passed through the gap.

The peak value of a diffraction X-ray frequently appears in a low angle region where an X-ray is incident to the sample mainly at a low angle. Therefore, it has been hitherto recognized that the gap between the sample and the X-ray shielding member or the shielding body should be adjusted in conformity with the width of the incident X-ray in the low angle region and it is less necessary for the X-ray shielding member or the shielding body to function sufficiently in a high angle region.

However, there are some materials for which the peak value of the diffraction X-ray also appears in a high angle region, and thus it has been required that the X-ray shielding member or the shielding body is made to effectively function over a broad region from the low angle region to the high angle region.

SUMMARY OF THE INVENTION

The present invention has been implemented in view of the foregoing situation, and has an object to provide an X-ray diffraction apparatus in which the gap between an X-ray incident face of a sample and an X-ray shielding member can be adjusted in conformity with variation of the width of the incident X-ray when the incident angle θ of the X-ray to a sample is changed.

In order to attain the above object, according to the present invention, an X-ray diffraction apparatus having a configuration that a divergence angle of an X-ray emitted from an X-ray source is limited by a divergence angle limiting unit, the X-ray is irradiated to an X-ray incident face of a sample held on a sample table and a diffraction X-ray diffracted from the sample is detected by an X-ray detector, a configuration that positional relationship corresponding to relative angular relationship of the X-ray source, the X-ray incident face of the sample held on the sample table and the X-ray detector is changed by a goniometer to change an incident angle of the X-ray to the sample, and the X-ray detector is disposed so as to face a diffraction direction of the diffraction X-ray diffracted from the sample, and a configuration that an X-ray shielding member is provided so as to confront the X-ray incident face of the sample so that a gap through which an incident X-ray emitted from the X-ray source and irradiated to the X-ray incident face of the sample can pass is formed between the X-ray shielding member and the X-ray incident face of the sample, comprises a gap adjusting unit that moves the X-ray shielding member in accordance with the change of the X-ray incident angle to the sample by the goniometer to adjust the breadth of the gap formed between the X-ray shielding member and the X-ray incident face of the sample in conformity with the width of the incident X-ray to the sample or the width for the diffraction direction of the diffracted X-ray from the sample.

According to the X-ray diffraction apparatus, the X-ray shielding member is moved in accordance with the change of the X-ray incident angle to the sample by the goniometer during execution of an X-ray diffraction measurement, and the breadth of the gap formed between the X-ray shielding member and the X-ray incident face of the sample is adjusted to a proper breadth conformed with the width of the incident X-ray or the diffraction X-ray. As a result, the incident X-ray is allowed to be incident to the sample without obstructing traveling of the incident X-ray and also traveling of scattered X-rays appearing around the incident X-ray can be effectively obstructed.

Here, the gap adjusting unit may comprise a guide support mechanism that is fixed to the sample table, and supports the X-ray shielding member to move and guide the X-ray shielding member in a direction perpendicular to the X-ray incident face of the sample, and a cam mechanism that moves the X-ray shielding member along the guide support mechanism.

For example, when the goniometer has an X-ray incident angle adjusting mechanism that changes positional relationship corresponding to relative angular relationship between the X-ray incident face of the sample held on the sample table and the X-ray source to change the incident angle of the X-ray to the sample, and a detector swing arm that is swung around the X-ray incident face of the sample while the X-ray detector is mounted thereon, whereby positional relationship corresponding to relative angular relationship between the X-ray incident face of the sample held on the sample table and the X-ray detector is changed to dispose the X-ray detector in the diffraction direction of the diffraction X-ray diffracted from the sample, the cam mechanism may be configured to have a cam fixed to the detector swing arm and a cam follower that is mounted on the X-ray shielding member and comes into contact with a cam face of the cam.

In this construction, the cam face of the cam is preferably shaped so as to move the X-ray shielding member in accordance with the change of the X-ray incident angle to the sample by the goniometer so that the breadth of the gap formed between the X-ray shielding member and the X-ray incident face of the sample is conformed with the width of the incident X-ray incident to the sample or the width of the diffraction X-ray diffracted from the sample.

Furthermore, the gap adjusting unit may be configured to have a guide support mechanism that is fixed to the sample table and guides the X-ray shielding member so that the X-ray shielding member is freely linearly movable so as to approach to and recede from the X-ray incident face of the sample, and a driving motor that drives the X-ray shielding member in accordance with the change of the X-ray incident angle to the sample by the goniometer so that the breadth of the gap formed between the X-ray shielding member and the X-ray incident face of the sample is conformed with the width of the incident X-ray incident to the sample or the width of the diffraction X-ray diffracted from the sample.

The gap adjusting unit is not limited to the above configurations, and it may have any configuration insofar as it can move the X-ray shielding member in accordance with the change of the X-ray incident angle to the sample by the goniometer, and the breadth of the gap formed between the X-ray shielding member and the X-ray irradiation face of the sample can be adjusted by the movement of the X-ray shielding member.

Furthermore, the X-ray shielding member may be a knife edge slit that is formed of a material through which X-rays never pass and designed in a plate-like shape having a sharp edge.

As described above, according to the present invention, when the positional relationship corresponding to the relative angular relationship of the X-ray source, the X-ray incident face of the sample held on the sample table and the X-ray detector is changed in connection with execution of an X-ray diffraction measurement, the gap between the X-ray incident face of the sample and the X-ray shielding member can be adjusted in conformity with the change of the width of the incident X-ray.

BRIEF DESCRIPTION OF THE DRAWINGS

FIG. 7 is a table showing specific data relating to the movement control of the X-ray shielding member by the gap adjusting mechanism (the movement control based on the cam mechanism);

FIG. 12 is a table showing specific data relating to the movement control of the X-ray shielding member by the gap adjusting mechanism (the movement control based on the cam mechanism);

FIG. 16 is a table representing specific data associated with the movement control of the X-ray shielding member (the movement control based on the cam mechanism) by the gap adjusting mechanism based on the irradiation width fixing method; and FIG. 17 is a table representing specific data associated with the movement control of the X-ray shielding member (the movement control based on the cam mechanism) by the gap adjusting mechanism based on the divergence angle fixing method.

DETAILED DESCRIPTION OF THE EMBODIMENTS

Preferred embodiments according to the present invention will be described with reference to the accompanying drawings.

Figure 1:
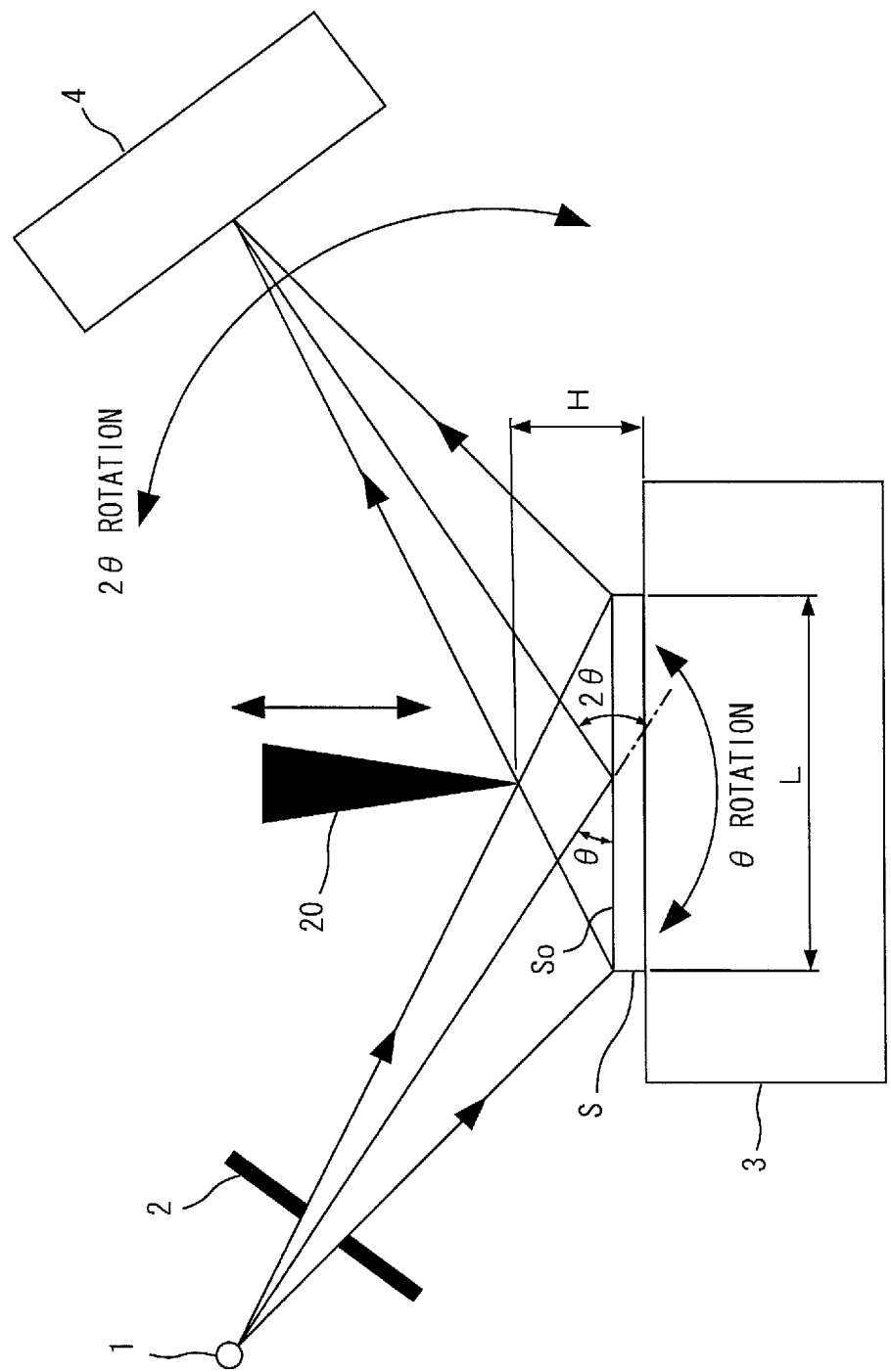
FIG. 1 is a diagram showing an X-ray diffraction apparatus according to an embodiment of the present invention.
Figure 2:
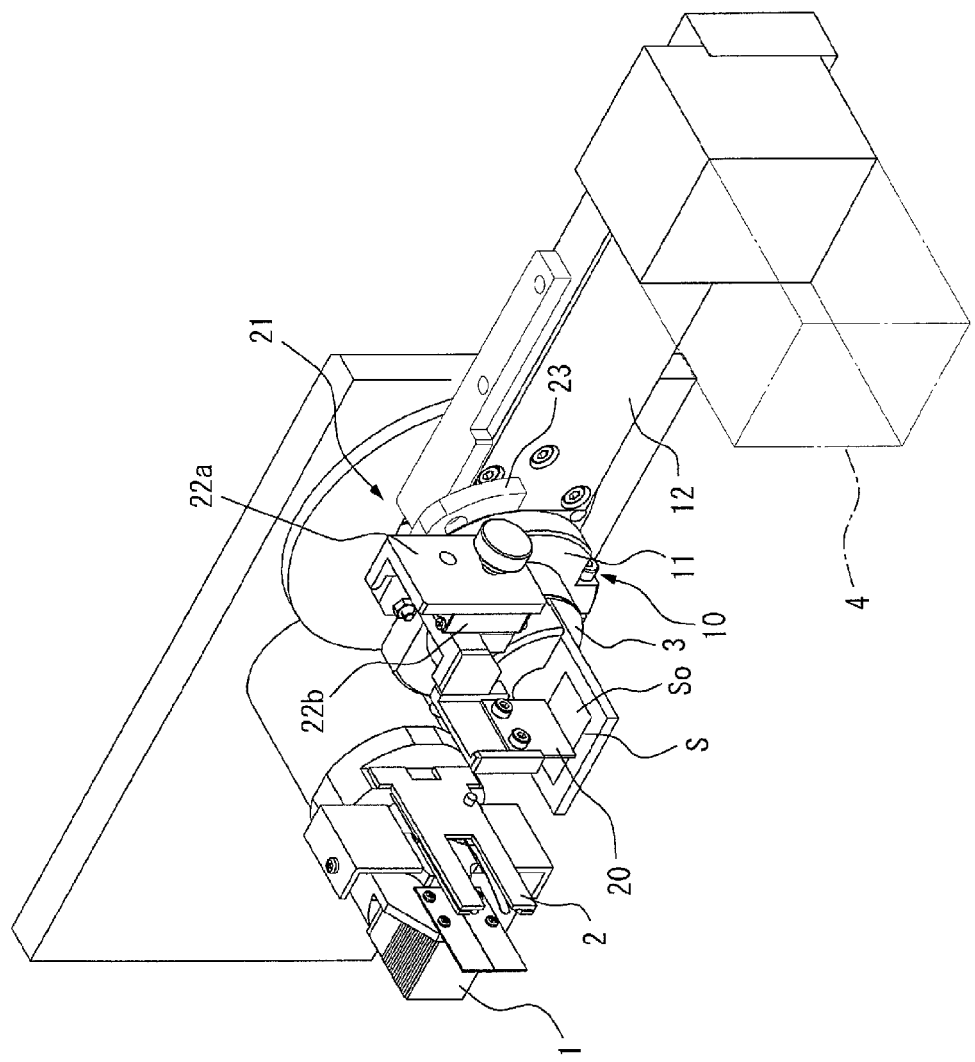
FIG. 2 is a perspective view showing a specific exterior configuration of the X-ray diffraction apparatus according to the embodiment of the present invention.
Figure 3:
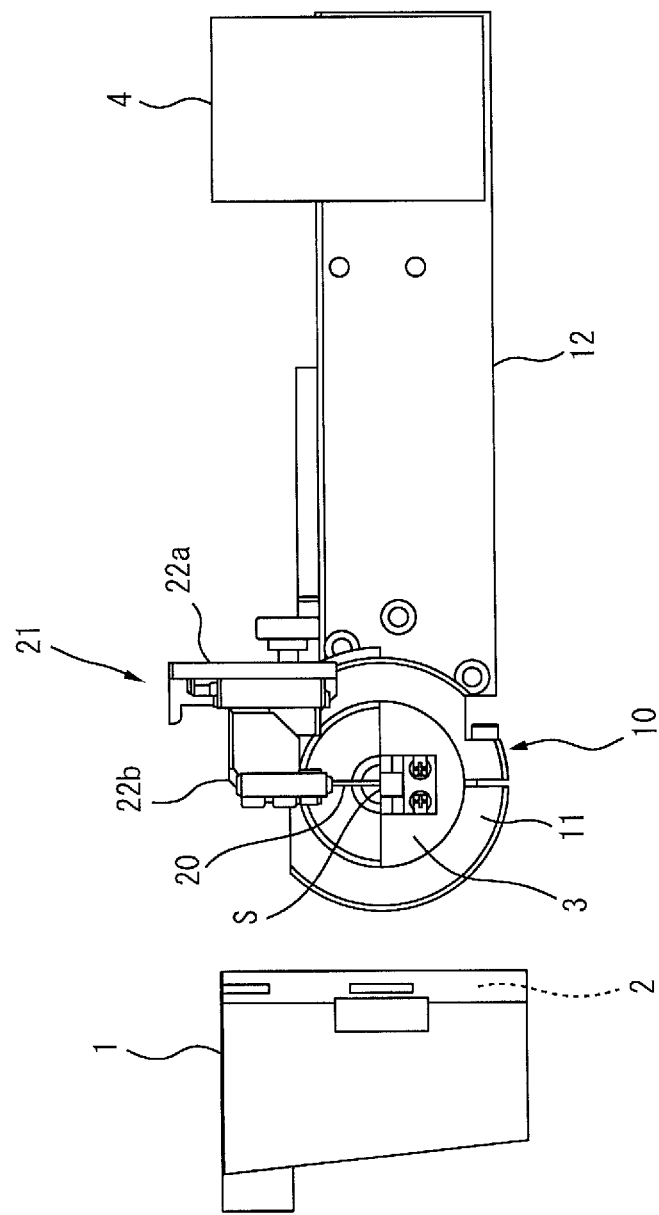
FIG. 3 is a front view showing the construction of a goniometer installed in the X-ray diffraction apparatus according to the embodiment of the present invention.

FIG. 1 is a diagram showing an X-ray diffraction apparatus according to an embodiment of the present invention, and FIG. 2 is a perspective view showing the specific exterior configuration of the X-ray diffraction apparatus.

As shown in FIGS. 1 and 2, the X-ray diffraction apparatus of this embodiment has an X-ray source 1 for emitting an X-ray, a divergence angle limiting slit 2 (diverging angle limiting unit) for limiting the divergence angle of the X-ray, a sample table 3 for holding a sample S, and an X-ray detector 4 for detecting a diffraction X-ray.

The divergence angle of an X-ray emitted from the X-ray source 1 is limited by the divergence angle limiting slit 2. As described hereinafter, there are two methods used for an X-ray diffraction measurement. One of the methods is an irradiation width fixing method in which the irradiation width L of an X-ray incident to an X-ray incident face of the sample S is fixed by changing the width of a slit during the X-ray diffraction measurement, and the other method is a divergence angle fixing method in which the divergence angle is limited to a fixed divergence angle by fixing the slit width during the X-ray diffraction measurement.

An X-ray which is emitted from the X-ray source 1 and whose divergence angle is limited by the divergence angle limiting slit 2 is irradiated to an X-ray incident face So of the sample S. As known publicly, when an X-ray is irradiated to the X-ray incident face So of the sample S at an angle of θ, a diffraction X-ray appears from the sample S in an angle direction of 2θ with respect to the incident X-ray. The angle 2θ at which the diffraction X-ray appears is determined by a material constituting the sample S, and thus the material constituting the sample S can be analyzed by detecting both the angle 2θ over which the diffraction X-ray appears, and the intensity of the diffraction X-ray.

The X-ray diffraction apparatus has the X-ray source 1 and a goniometer 10 to perform an X-ray diffraction measurement while changing the positional relationship corresponding to the relative angular relationship between the X-ray incident face So of the sample S mounted on the sample table 3 and the X-ray detector 4 (see FIG. 2). The construction of the goniometer 10 will be described in detail later. The incident angle θ of the X-ray from the X-ray source 1 to the X-ray incident face So of the sample S is adjusted by the goniometer 10, and the X-ray detector 4 is disposed to be swung in the direction of the angle 2θ with respect to the incident X-ray (that is, the direction from which the diffraction X-ray diffracted from the sample S appears).

Furthermore, the X-ray diffraction apparatus is provided with an X-ray shielding member 20 which is disposed so as to confront the X-ray incident face So of the sample S. The material of the X-ray shielding member 20 is not limited to a specific material insofar as X-rays are never passed through the material. For example, it may be formed of brass, a steel product, lead or the like. The shape of the X-ray shielding member 20 is not limited to a specific shape. When it is formed of a plate-like member, this is favorable because it does not need a large mounting space. In general, the X-ray shielding member 20 is called as a knife edge slit, and it is frequently processed so that the edge of a plate member is configured in a sharp wedge shape.

The X-ray shielding member 20 forms a gap H between itself and the X-ray incident face So of the sample S so that an incident X-ray which is emitted from the X-ray source 1 to be irradiated to the X-ray incident face So of the sample can pass through the gap H concerned.

In addition, the X-ray diffraction apparatus is also provided with a gap adjusting mechanism 21 (gap adjusting unit) for adjusting the breadth of the gap H formed between the X-ray shielding member 20 and the X-ray incident face So of the sample S by moving the X-ray shielding member 20 in a direction perpendicular to the X-ray incident face So of the sample S in connection with the change of the X-ray incident angle θ to the sample S with the goniometer 10 during execution of the X-ray diffraction measurement (see FIG. 2).

As described above, when the X-ray incident angle θ to the sample S is changed, the width of the incident X-ray varies in connection with the change of the incident angle θ at the confronting position at which the X-ray shielding member 20 confronts the sample S. The X-ray shielding member 20 has a function of adjusting the breadth of the gap H formed between the X-ray shielding member 20 and the X-ray incident face So of the sample S in accordance with the variation of the width of the incident X-ray which occurs due to the change of the incident angle θ.

The gap H formed between the X-ray shielding member 20 and the X-ray incident face So of the sample S is adjusted in conformity with the width of the incident X-ray passing through the gap H by the actuation of the gap adjusting mechanism 21.

Next, the gap adjusting mechanism 21 installed in the goniometer 10 will be described with reference to FIGS. 2 to 5.

The goniometer 10 has a θ rotating disc 11 as an X-ray incident angle adjusting mechanism, and a 2θ swing arm 12 as a detector swing arm. The θ rotating disc 11 and the 2θ swing arm 12 are configured to rotate/swing around the same rotational axis so that when the θ rotating disc 11 rotates by only an angle of θ, the 2θ swing arm 12 swings around the same rotational axis by only an angle of 2θ interlockingly with the rotation of the θ rotating disc 11.

A sample table 3 is mounted on the θ rotating disc 11 and the sample S is held on the sample table 3. The sample table 3 is rotated in connection with the rotation of the θ rotating disc 11, thereby changing the positional relationship corresponding to the relative angle between the X-ray source 1 and the X-ray incident face So of the sample S held on the sample table 3. Accordingly, the incident angle of the X-ray to the sample S is changed.

The X-ray detector 4 is mounted on the 2θ swing arm 12. The X-ray detector 4 swings around the X-ray incident face So of the sample S together with the 2θ swing arm. Accordingly, the positional relationship corresponding to the relative angle between the X-ray detector 4 and the X-ray incident face So of the sample S held on the sample table 3 is changed, and the X-ray detector 4 is moved to a position at which the diffraction X-ray diffracted from the sample S is detected.

In this embodiment, the gap adjusting mechanism 21 is constructed by a cam mechanism. That is, the gap adjusting mechanism 21 contains a guide support mechanism 22, a cam 23 and a cam follower 24. The guide support mechanism 22 is configured so that a slider 22b is freely slidably installed in a support plate 22a fixed to the sample table 3, and the X-ray shielding member 20 is mounted on the slider 22b. The moving direction of the slider 22b is set to a direction perpendicular to the X-ray incident face So of the sample S. The X-ray shielding member 20 is reciprocated in the direction perpendicular to the X-ray incident face So of the sample S together with the slider 22b.

Figure 4:
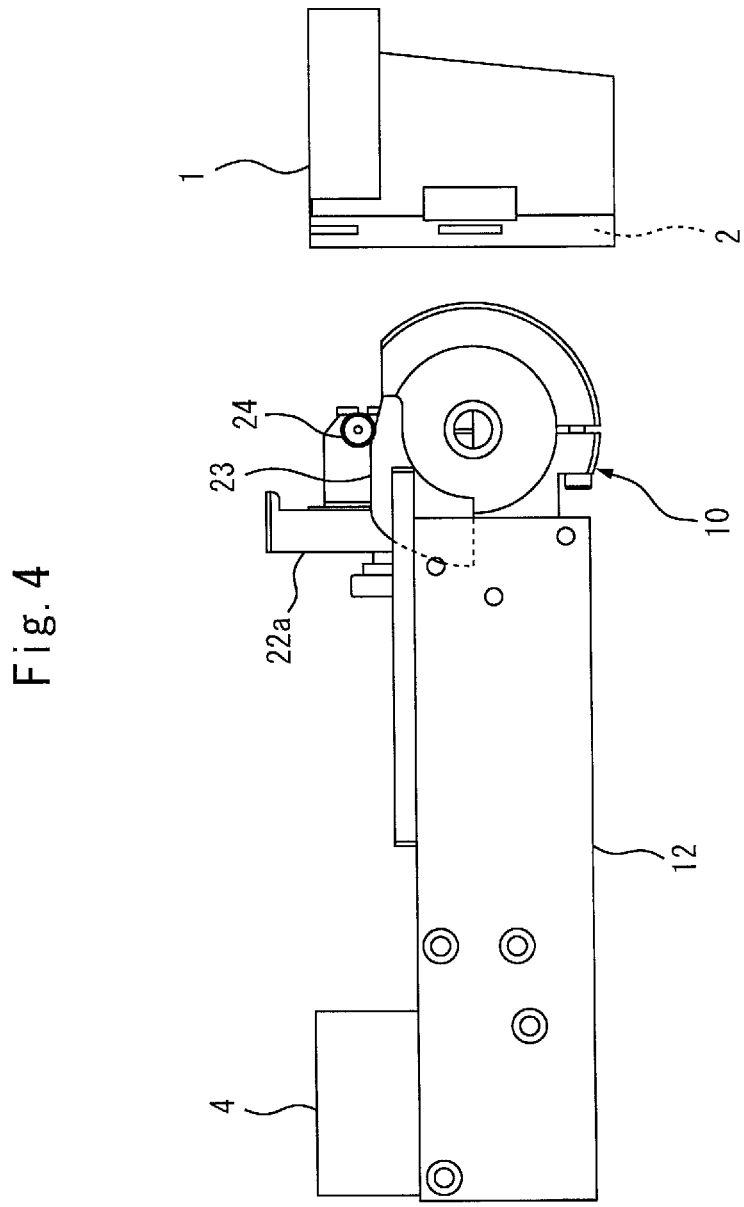
FIG. 4 is a back view showing the construction of the goniometer.
Figure 5:
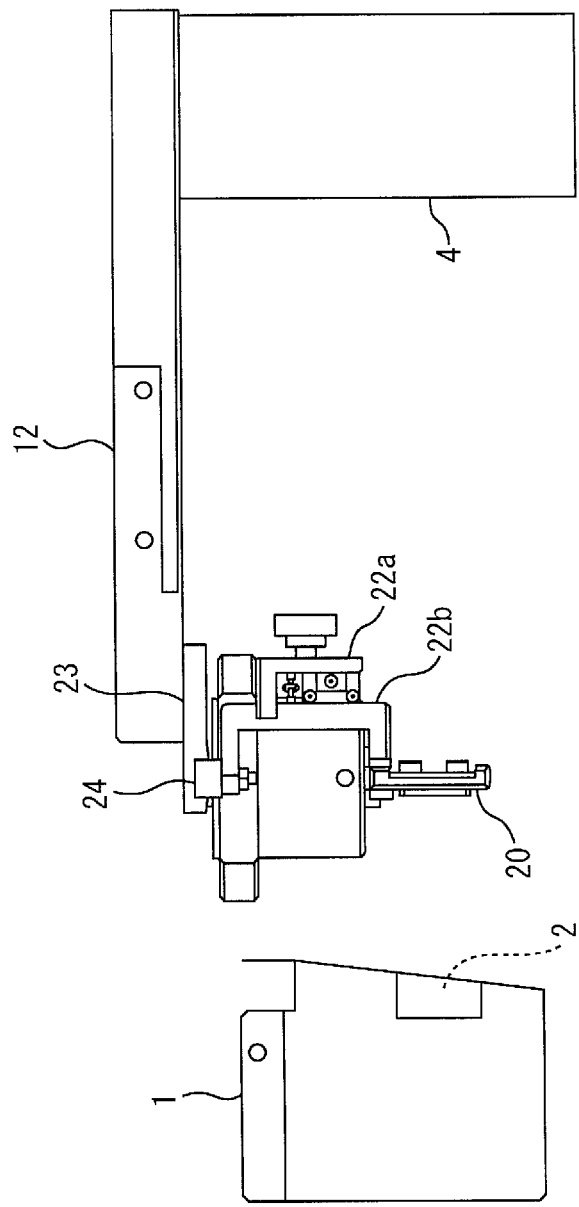
FIG. 5 is a plan view showing the construction of the goniometer.

The cam 23 is fixed to the 2θ swing arm 12, and actuated interlockingly with the swing operation of the 2θ swing arm 12 (see FIG. 4). The cam follower 24 is mounted on the back surface of the slider 22b (see FIGS. 4 and 5). This cam follower 24 comes into contact with a cam face formed on the cam 23. Accordingly, when the cam 23 is activated together with the 2θ swing arm 12, the cam follower 24 linearly moves together with slider 22b on the basis of the shape of the cam face. The X-ray shielding member 20 is mounted on the slider 22b, and thus the movement of the X-ray shielding member 20 directly corresponds to the movement of the cam follower 24.

The cam face of the cam 23 is processed to have such a shape that the X-ray shielding member 20 is moved so that the gap H between the X-ray shielding member 20 and the X-ray incident face So of the sample S is conformed with the width of the incident X-ray passing through the gap H concerned.

Next, construction examples of the cam face formed on the cam 23 will be described mainly with reference to FIGS. 6 to 11.

In this embodiment, there will be separately described a construction example of the cam face suitable to a case where an X-ray diffraction measurement is performed on the basis of the so-called "irradiation width fixing method" in which the irradiation width L of the X-ray incident to the X-ray incident face So of the sample S is fixed, and another construction example of the cam face suitable to a case where an X-ray diffraction measurement is performed on the basis of the so-called "divergence angle fixing method" in which the divergence angle of the X-ray emitted from the X-ray source and incident to the X-ray incident face So of the sample is set to be fixed.

[Construction Example of Cam Face based on Irradiation Width Fixing Method]

Figure 6:
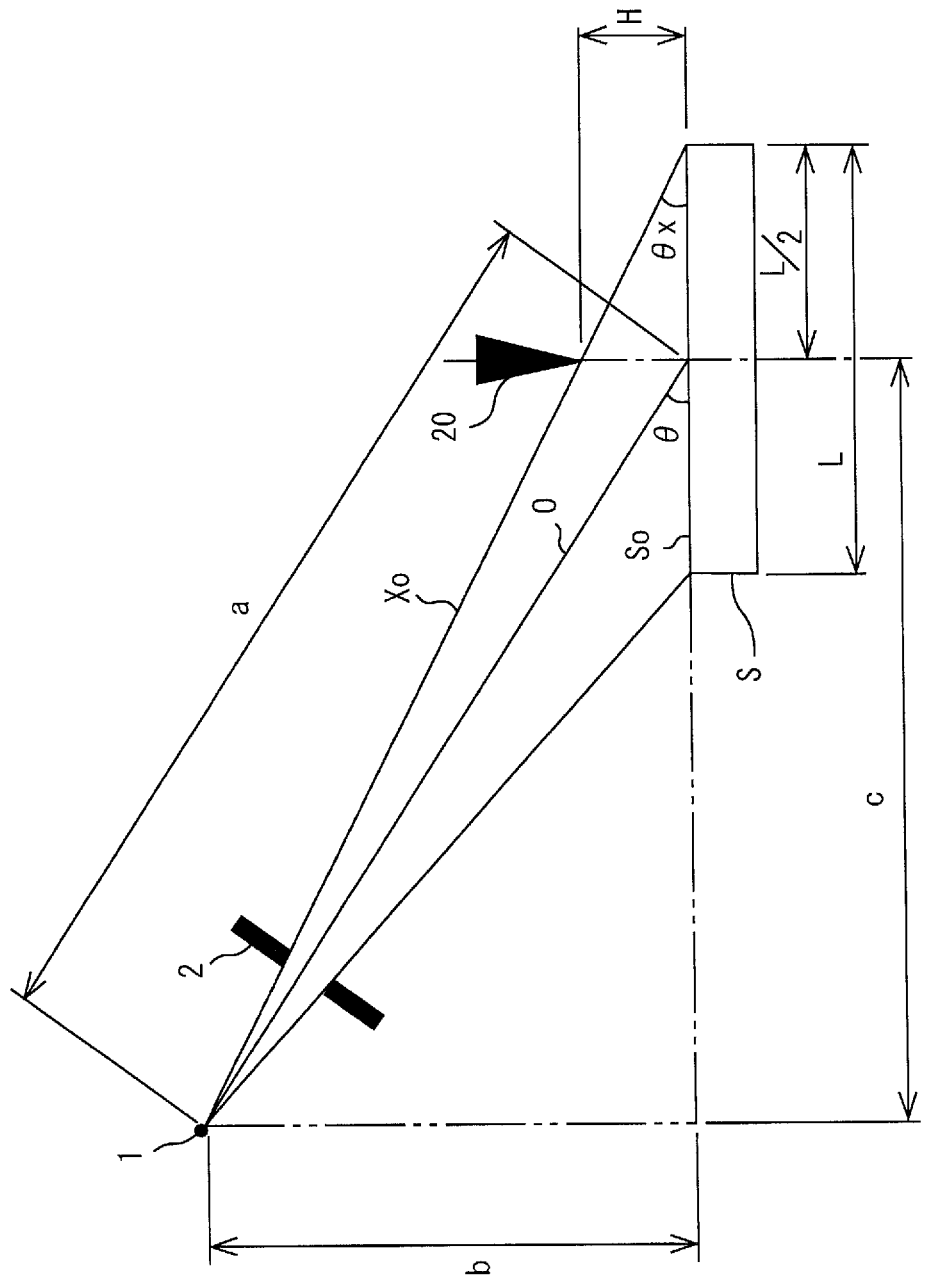
FIG. 6 is a diagram showing control of movement of an X-ray shielding member by a gap adjusting mechanism (movement control based on a cam mechanism) when an X-ray diffraction measurement is executed according to an irradiation width fixing method.

According to the irradiation width fixing method, as shown in FIG. 6, the slit width of the divergence angle limiting slit 2 is changed in accordance with the change of the X-ray incident angle θ to the X-ray incident face So of the sample S so that the irradiation width L of the X-ray incident to the X-ray incident face So of the sample S is fixed. A mechanism for actuating the divergence angle limiting slit 2 as described above interlockingly with rotation of the sample S has been disclosed in JP-A-8-262196, for example.

According to the irradiation width fixing method, an axis connecting the center of the X-ray source 1 and the center (the position of L/2) of an X-ray (an incident X-ray) having an irradiation width L irradiated to the X-ray incident face So of the sample S is set as a reference axis O, and the intersection angle between the X-ray source 1 and the rotational center of the goniometer 10, i.e., the intersection angle between the reference axis O and the X-ray incident face So at the rotational center of the goniometer 10 is defined as an incident angle θ. The goniometer 10 is disposed so that the rotational center of the goniometer 10 is coincident with the center of the irradiation width L of the incident X-ray (the position of L/2), and rotates (swings) the sample S and the X-ray detector 4.

Here, the X-ray shielding member 20 is set so as to confront the center of the irradiation width L on the X-ray incident face So of the sample S and further approach to and recede from the X-ray incident face So of the sample S in the direction perpendicular to the X-ray incident face So of the sample S at the confronting position. A gap H for allowing the incident X-ray to pass therethrough is formed between the X-ray shielding member 20 and the X-ray incident face So of the sample S.

When the intersection angle between the X-ray incident face So of the sample S and the outer edge Xo of an incident X-ray incident to a position farthest from the X-ray source 1 on the X-ray incident face So of the sample S (see FIG. 6) is represented by θx, the following relational expression is satisfied between the angle θx and the gap H.

$$\tan(\theta x) = H/(L/2)$$

$$H = \tan(\theta x) \times (L/2) \quad (1)$$

The cam face of the cam 23 in the gap adjusting mechanism 21 is shaped so that the X-ray shielding member 20 is moved so as to form the gap H on the basis of the relational expression described above.

The angle θX is a function of the incident angle θ of the X-ray to the X-ray incident face So of the sample S, and it can be calculated from the incident angle θ. For example, it can be geometrically calculated by using a right triangle defined by the locus of the reference axis O extending from the X-ray source 1 to the X-ray incident center position (L/2) of the sample S, a virtual plane containing the X-ray incident plane So of the sample S and the perpendicular line dropped from the X-ray source 1 to the virtual plane. When the lengths of the respective sides of this triangle are represented by a, b and c as shown in FIG. 6, the length a is fixed, and the lengths b and c vary in accordance with the incident angle θ and can be calculated by using a trigonometric function of θ.

The angle (θx) can be calculated from the following relational expression (2).

$$\tan(\theta x)=b/\{c+(L/2)\} \quad (2)$$

FIG. 7 is a table showing calculation results of the above respective values with respect to the variation of the incident angle θ when the distance a from the X-ray source 1 to the position (the position of L/2) at which the reference axis O of the incident X-ray is incident to the sample S is set to 150 mm and the irradiation width of the X-ray incident to the X-ray incident face So of the sample S is set to 20 mm.

Figure 8:
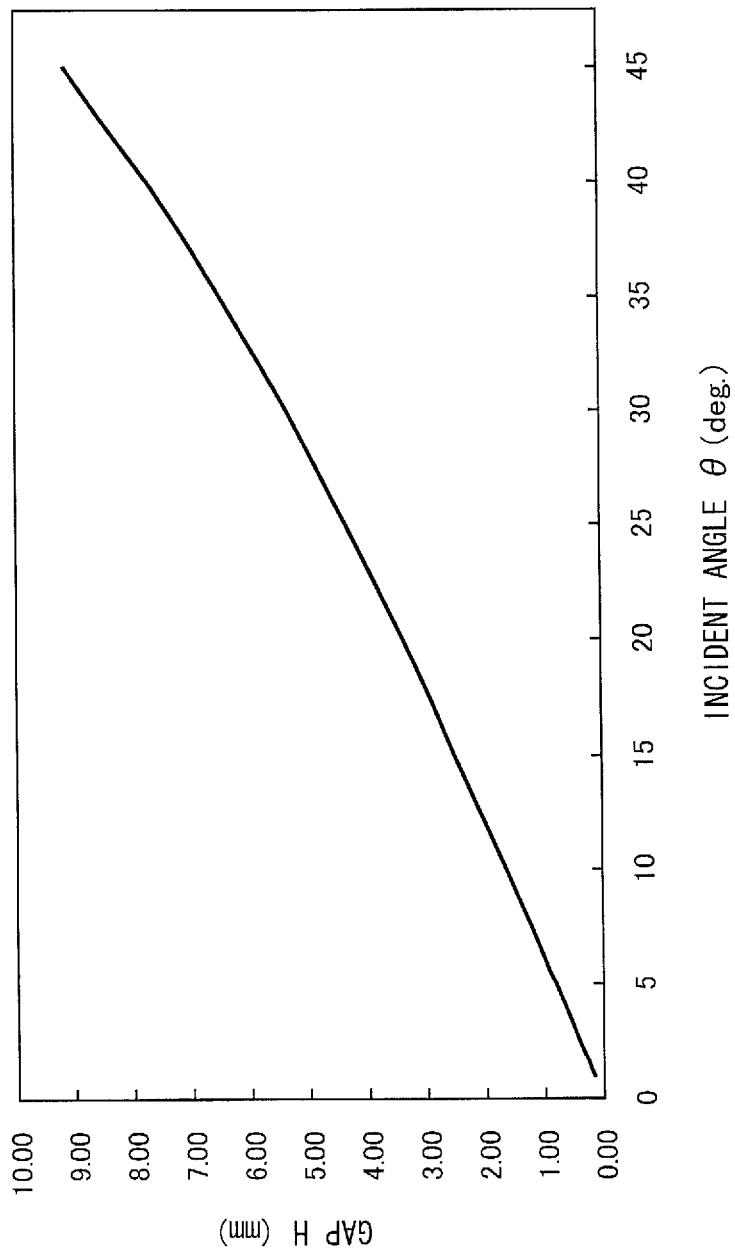
FIG. 8 is a graph showing the specific data relating to the movement control of the X-ray shielding member by the gap adjusting mechanism (the movement control based on the cam mechanism)

FIG. 8 is a graph showing the relationship between the incident angle θ and the gap H based on the calculation results of FIG. 7. The cam face of the cam 23 of the gap adjusting mechanism 21 may be designed so that the gap H varies with the variation of the incident angle θ according to this relationship.

As shown in FIG. 1, these designs are particularly of to an X-ray optical system in which the diffraction X-ray from the sample S is converged to one point on the X-ray detector 4.

Figure 9:
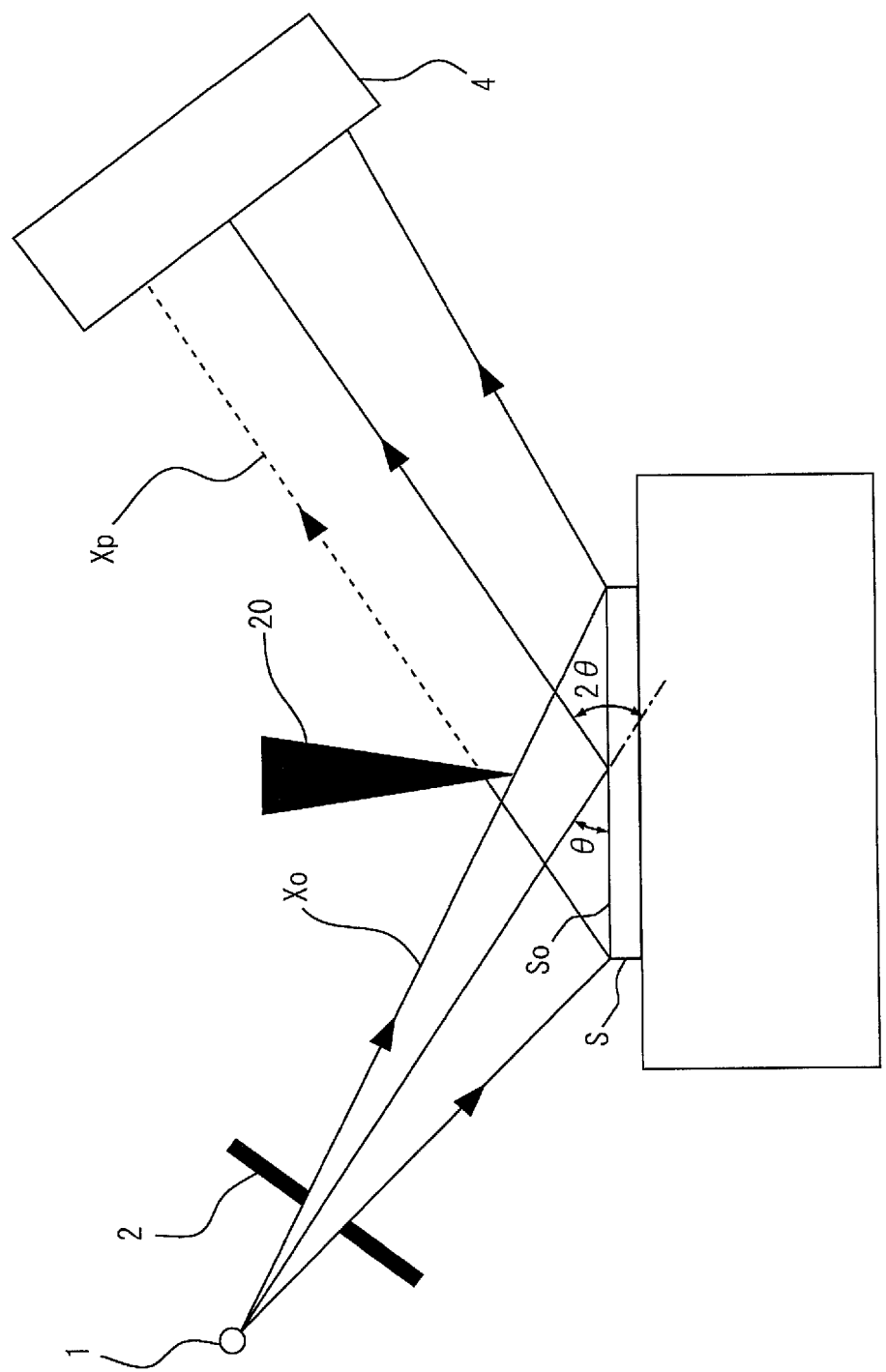
FIG. 9 is a diagram showing a phenomenon that the outer edge at a wide angle side of a diffraction X-ray is shielded by the X-ray shielding member.

However, in the case of an X-ray optical system using an X-ray detector having one-dimensional angular resolution capability, the calculated gap H may bring a probability that the outer edge Xp at a wide angle side of a diffraction X-ray diffracted from the sample S is shielded by the X-ray shielding member 20 as shown in FIG. 9. Therefore, when the cam face is formed, it is preferable that the position of the X-ray shielding member 20 is finely adjusted (offset) on the basis of the calculated gap H so that the outer edge Xp at the wide angle side of the diffraction X-ray diffracted from the sample S is not shielded by the X-ray shielding member 20.

Figure 10:
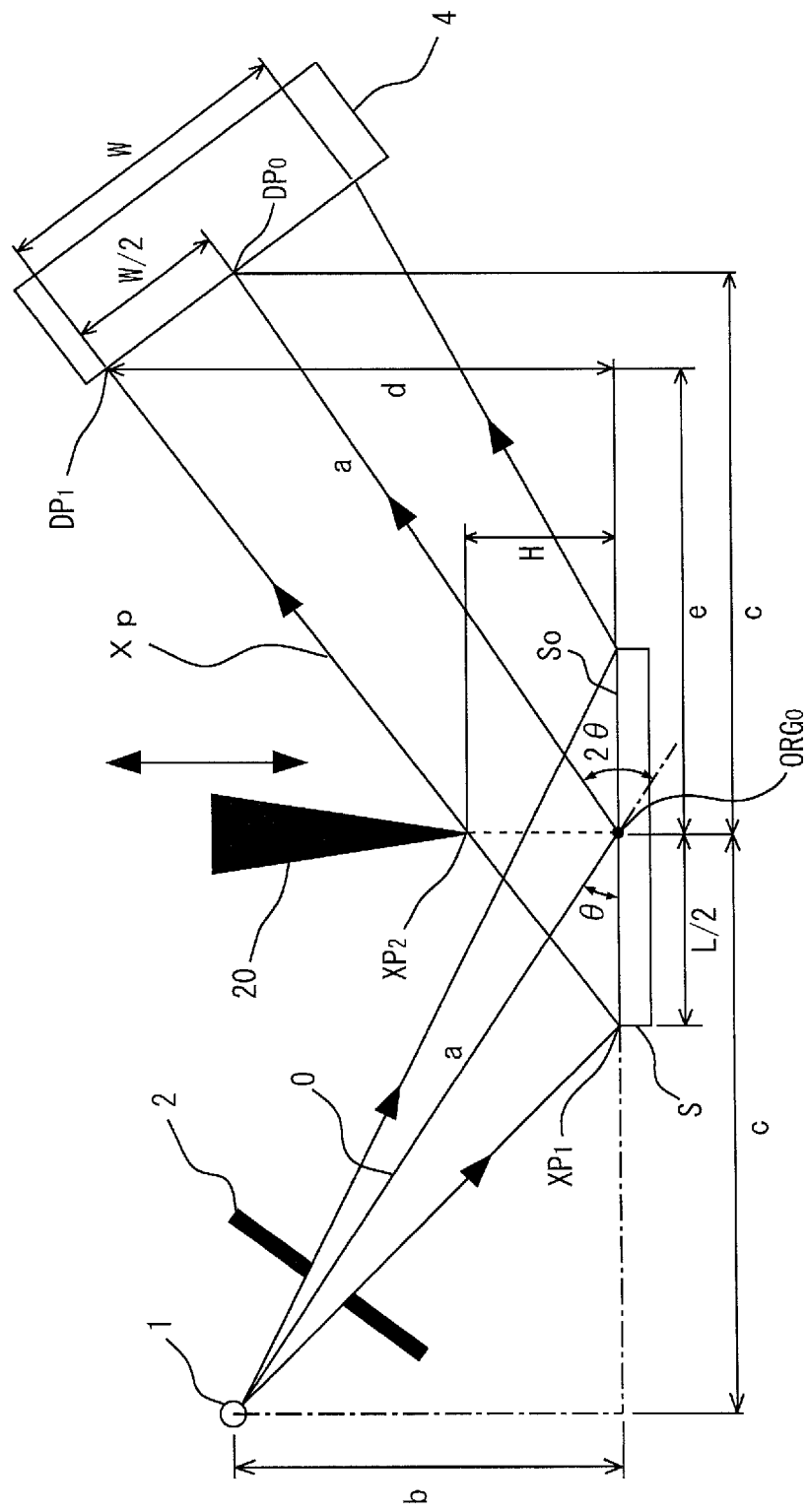
FIG. 10 is a diagram showing another movement control of the X-ray shielding member by the gap adjusting mechanism (movement control based on the cam mechanism) when the X-ray diffraction measurement is executed according to the irradiation fixing method.

Furthermore, as shown in FIG. 10, the breadth of the gap H formed between the X-ray shielding member and the X-ray incident face of the sample may be adjusted in conformity with the width of the incident X-ray incident to the sample or the width of the diffraction X-ray diffracted from the sample.

That is, the cam face of the cam 23 may be shaped so as to move the X-ray shielding member so that the gap H formed between the X-ray shielding member 20 and the X-ray incident face So of the sample S is conformed with the width of the diffraction X-ray passing through the gap H.

In this case, when the effective width of an X-ray incident window in the X-ray detector 4 is represented by W, the center position of the X-ray incident window is represented by $DP_0$, and the end position at a high angle side of the diffraction angle is represented by $DP_1$, the distance between $DP_0$ and $DP_1$ is equal to W/2.

Here, there are assumed a right triangle whose apexes correspond to an X-ray incident end position $XP_1$ (the left end position of FIG. 10) of the sample S, the tip position $XP_2$ of the X-ray shielding member 20 and an X-ray incident center position $ORG_0$ of the sample S, and also a right triangle which is similar to the above right triangle and whose apexes correspond to $XP_1$ and $DP_1$. The gap H can be calculated in consideration of the similarity relationship between these triangles.

That is, when the distance from $ORG_0$ to $DP_0$ is represented by R, the position of $DP_1$ can be calculated from the following mathematical expression (3), wherein d represents the distance from $ORG_0$ to the Y-coordinate (the vertical coordinate of FIG. 10) of $DP_1$ and e represents the distance from $ORG_0$ to the X-coordinate (the lateral coordinate of FIG. 10) of $DP_1$.

$$d = R \times \sin\theta + (W/2) \times \cos\theta$$

$$e = R \times \cos\theta + (W/2) \times \sin\theta \quad (3)$$

Here, when it is assumed that the distance R from $ORG_0$ to $DP_0$ is equal to the distance a from the X-ray source 1 to $ORG_0$, the gap H can be calculated from the following mathematical expression (4).

$$H = \frac{(L/2) \times (a \times \sin\theta + (W/2) \times \cos\theta)}{(L/2) + (a \times \cos\theta - (W/2) \times \sin\theta)} \quad (4)$$

FIG. 16 shows a calculation result of the gap H based on the mathematical expression (4) when W/2 is set to 6.4 mm.

[Construction Example Based on Divergence Angle Fixing Method]

Figure 11:
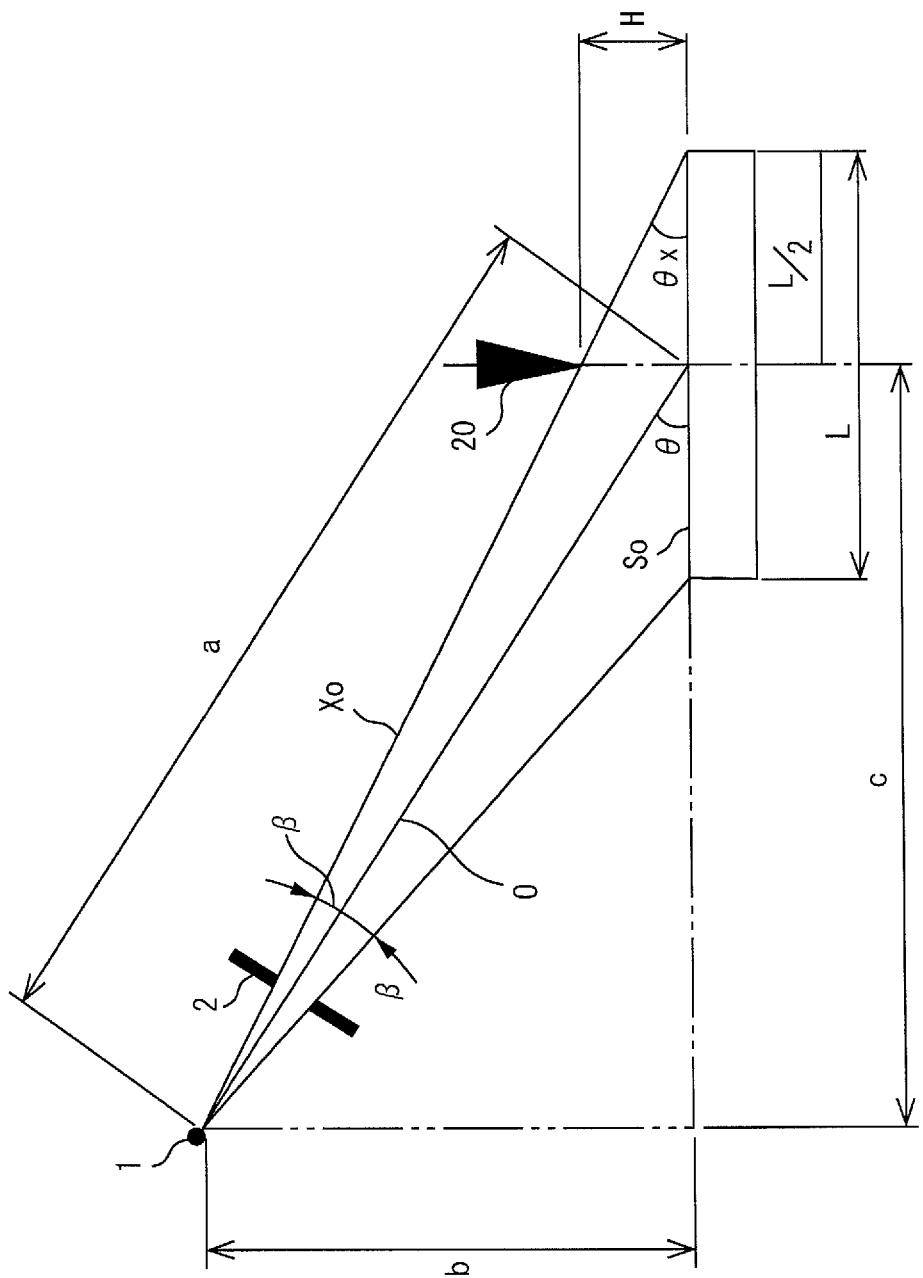
FIG. 11 is a diagram showing the movement control of the X-ray shielding member by the gap adjusting mechanism (the movement control based on the cam mechanism) when an X-ray diffraction measurement is executed according to a divergence angle fixing method.

According to the divergence angle fixing method, as shown in FIG. 11, the slit width of the divergence angle limiting slit 2 is fixed so that the divergence angle β of an X-ray which is emitted from the X-ray source 1 and incident to the X-ray incident face So is fixed. Accordingly, the irradiation width L of the X-ray on the X-ray incident face So of the sample S varies in accordance with change of the incident angle θ.

According to the divergence angle fixing method, the locus of an X-ray traveling at the center of the divergence angle (β/2) is represented as a reference axis O, and the incident angle θ is defined by the intersection angle between the reference axis O and the X-ray incident face of the sample s at the rotational center of the goniometer 10 (the center of the X-ray incident face So).

As in the case of the irradiation width fixing method, the X-ray shielding member 20 is set so as to confront the center of the irradiation width L on the X-ray incident face So of the sample S and further approach to and recede from the X-ray incident face So of the sample S in the direction perpendicular to the X-ray incident face So of the sample S at the confronting position. The gap H through which an incident X-ray is passed is formed between the X-ray shielding member 20 and the X-ray incident face So of the sample S.

Furthermore, when the intersection angle between the X-ray incident face So of the sample S and an outer edge Xo of an incident X-ray which is incident to a position farthest from the X-ray source 1 on the X-ray incident face So of the sample S is represented by θx, the following relationship is satisfied between the angle θx and the gap H as in the case of the irradiation width fixing method.

$$\tan(\theta x) = H/(L/2)$$

$$H = \tan(\theta x) \times (L/2) \quad (5)$$

The cam face of the cam 23 in the gap adjusting mechanism 21 is shaped to move the X-ray shielding member 20 so that the gap H is formed on the basis of this relational expression.

Here, the angle θx is a function of the X-ray incident angle θ to the X-ray incident face So of the sample S, and it can be calculated from the incident angle θ. For example, from the total of the inner angles of a triangle defined by the outer edge Xo of an incident X-ray incident to a position farthest from the X-ray source 1 on the X-ray incident face So of the sample S, the reference axis O and the X-ray incident face So of the sample S, the following relationship is derived.

$$(\beta/2)+(\theta x)+(180-\theta)=180$$

$$(\beta/2)+(\theta x)-\theta=0 \quad (b\ 6)$$

θx can be calculated from this relational expression.

FIG. 12 is a table showing calculation results of the above respective values with respect to the variation of the incident angle θ when the distance a from the X-ray source 1 to the position at which the reference axis O of the incident X-ray intersects to the sample S is set to 150 mm and the divergence angle β of the incident X-ray is set to 1°.

Figure 13:
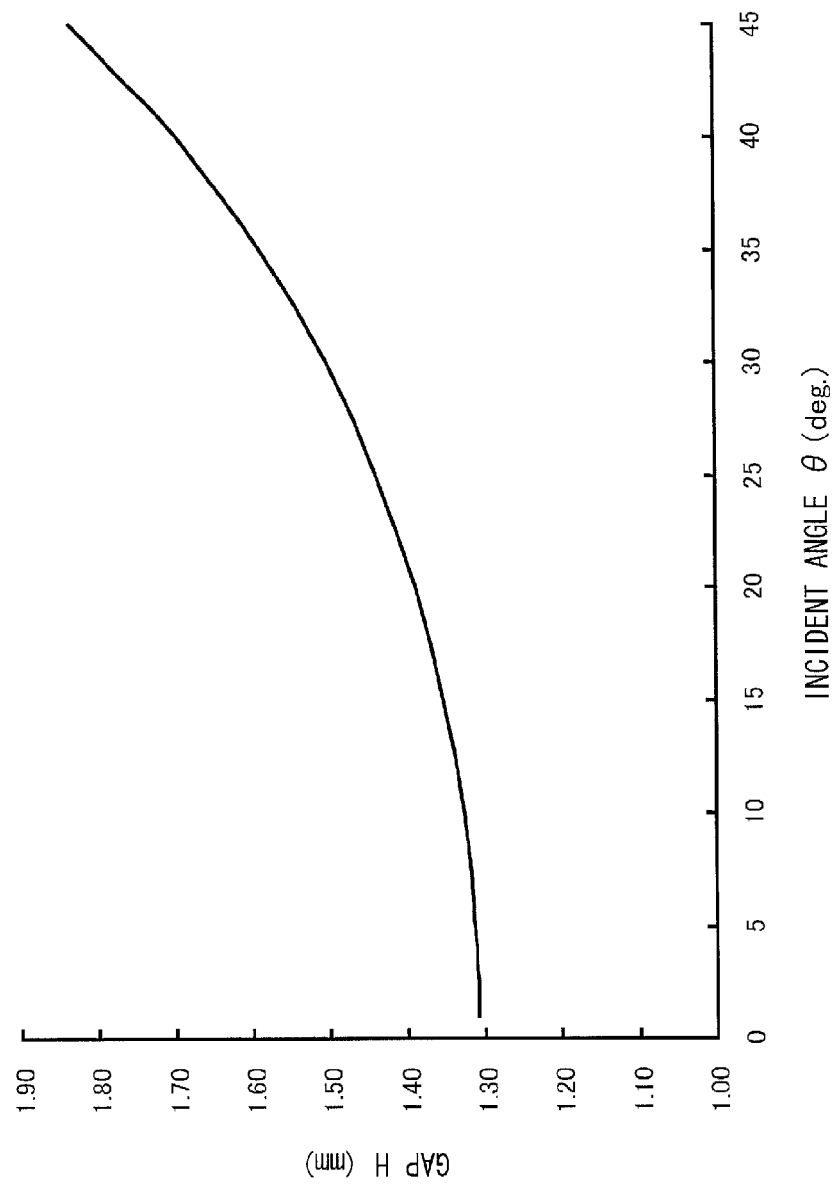
FIG. 13 is a graph showing specific data relating to the movement control of the X-ray shielding member by the gap adjusting mechanism (the movement control based on the cam mechanism)

FIG. 13 is a graph showing the relationship between the incident angle θ and the gap H based on the calculation results shown in FIG. 12. The cam face of the cam 23 in the gap adjusting mechanism 21 may be designed so that the gap H varies with the change of the incident angle θ according to the above relationship.

In the divergence angle fixing method, the calculated gap H may also bring a probability that the outer edge Xp at a wide angle side of a diffraction X-ray diffracted from the sample S is shielded by the X-ray shielding member 20 as shown in FIG. 9. Therefore, when the cam face is formed, it is preferable that the position of the X-ray shielding member 20 is finely adjusted (offset) on the basis of the calculated gap H so that the outer edge Xp at the wide angle side of the diffraction X-ray diffracted from the sample S is not shielded by the X-ray shielding member 20.

Figure 14:
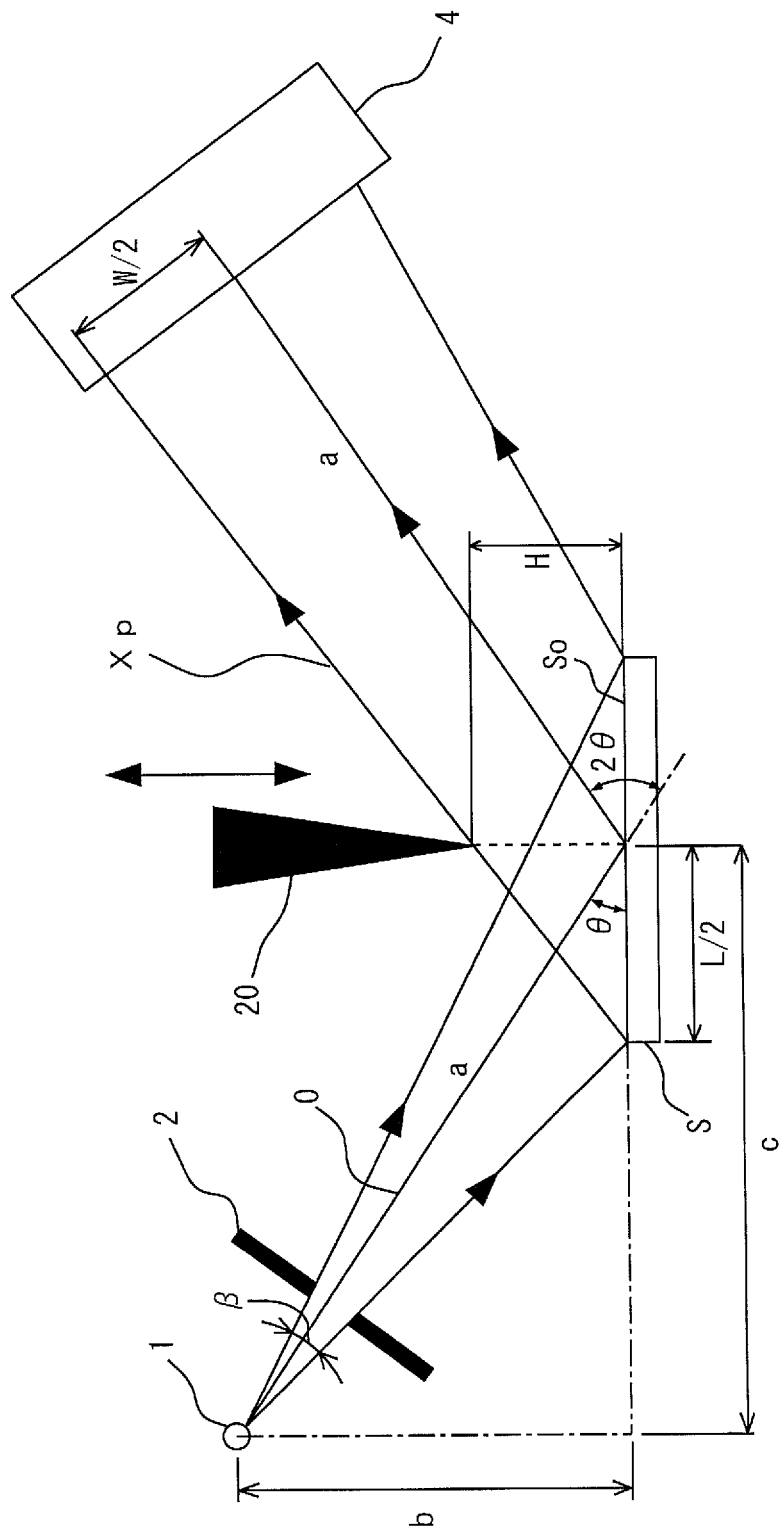
FIG. 14 is a diagram showing another control movement of the X-ray shielding member by the gap adjusting mechanism (movement control based on the cam mechanism) when the X-ray diffraction measurement is executed according to the divergence angle fixing method.

Furthermore, as shown in FIG. 14, the breadth of the gap H formed between the X-ray shielding member and the X-ray incident face of the sample may be adjusted in conformity with the width of the incident X-ray incident to the sample or the width of the diffraction X-ray diffracted from the sample.

That is, the cam face of the cam 23 may be shaped so as to move the X-ray shielding member so that the gap H formed between the X-ray shielding member 20 and the X-ray incident face So of the sample S is conformed with the width of the diffraction X-ray passing through the gap H.

In this case, when the outer edge Xp of the diffraction X-ray diffracted from the sample S and the gap H satisfy the following relationship as in the case of the irradiation width fixing method:

$$H = \frac{(L/2) \times (a \times \sin\theta + (W/2) \times \cos\theta)}{(L/2) + (a \times \cos\theta - (W/2) \times \sin\theta)} \quad (7)$$

The cam face of the cam 23 in the gap adjusting mechanism 21 may be shaped so as to move the X-ray shielding member 20 so that the gap H is formed on the basis of this relational expression (7).

Here, the irradiation width on the sample S when the sample S is irradiated with X-ray at a divergence angle of β/2 from the center position of the sample is represented by the following mathematical expression at the side nearer to the X-ray source 1 (see FIG. 14).

$$L/2 = a \times \cos\theta - [(a \times \sin\theta)/\tan\{\theta - (\beta/2)\}] \quad (8)$$

Furthermore, the irradiation width is represented by the following mathematical expression at the side farther from the X-ray source 1 (see FIG. 11).

$$L/2 = [(a \times \sin\theta)/\tan\{\theta - (\beta/2)\}] - a \times \cos\theta \quad (9)$$

As shown in FIG. 14, the mathematical expression (8) may be used in this example.

FIG. 17 shows a calculation result of the gap H based on the mathematical expressions (7) and (8) when W/2 is set to 6.4 mm.

Figure 15:
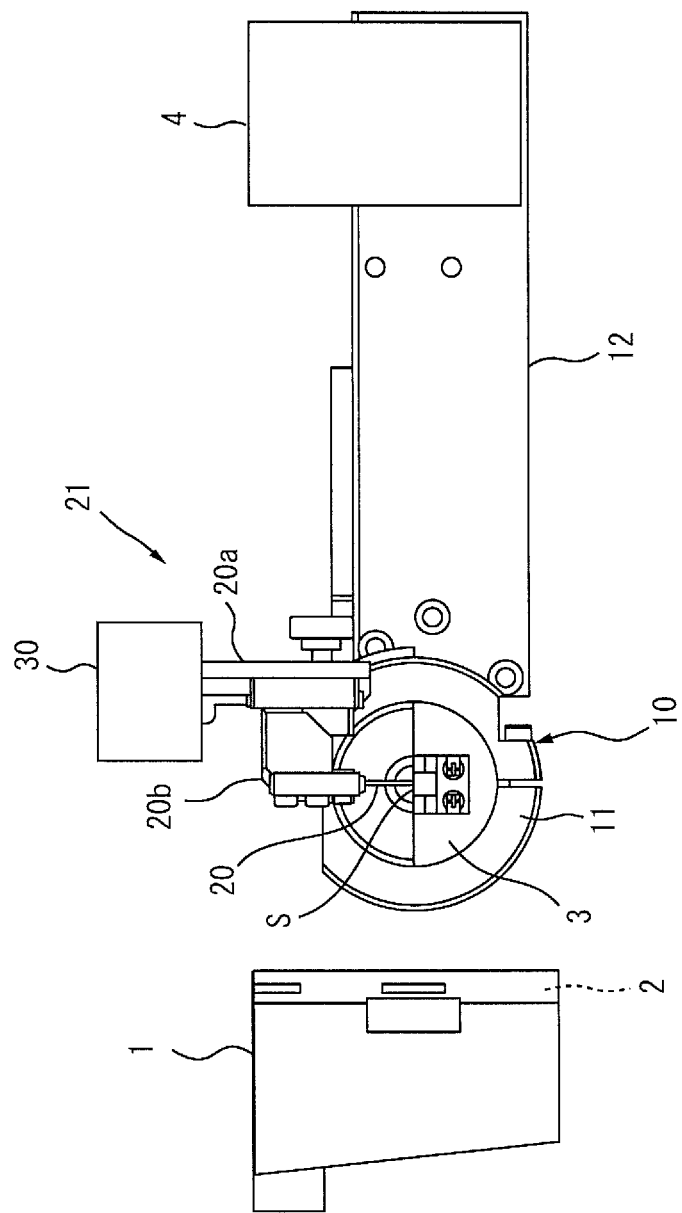
FIG. 15 is a front view showing an X-ray diffraction apparatus according to another embodiment of the present invention.

FIG. 15 is a diagram showing the construction of an X-ray diffraction apparatus according to another embodiment of the present invention.

In the embodiment shown in FIG. 15, the gap adjusting mechanism is configured so that the X-ray shielding member 20 is moved by using a driving motor 30.

That is, the gap adjusting unit contains a guide support mechanism 22 and a driving motor 30. The guide support mechanism 22 is configured so that a slider member 22b is freely slidably mounted on a support plate 22a fixed to a sample table 3 and an X-ray shielding member 20 is mounted on the slider 22b as in the case of the foregoing embodiment. The moving direction of the slider 22b is set to a direction perpendicular to the X-ray incident face So of the sample S. The X-ray shielding member 20 reciprocates in the direction perpendicular to the X-ray incident face So of the sample S together with the slider 22b.

Furthermore, the driving motor 30 is mounted on the support plate 22a. The driving force of the driving motor 30 is transmitted to the slider 22b though a power transmission mechanism (not shown) to move the slider 22b. Various kinds of publicly known mechanisms such as a ball screw mechanism, a gear mechanism, etc. may be applied as the power transmission mechanism.

The operation of the driving motor 30 is controlled by a controller (not shown). The operation control of the driving motor 30 is performed on the basis of the relational expression (1) or (5) satisfied between the angle θx and the gap H, wherein the angle θx is the intersection angle between the X-ray incident face So of the sample S and the outer edge Xo of the incident X-ray incident to the position farthest from the X-ray source 1 on the X-ray incident face So of the sample S, and the gap H is a gap formed between the X-ray shielding member 20 and the sample S as described above.

Furthermore, the operation control of the driving motor 30 may be performed on the basis of the relational expression (3) or (7) satisfied between the angle θp and the gap H, wherein the angle θp is the intersection angle between the X-ray incident face So of the sample S and the outer edge Xp at the wide angle side of the diffraction X-ray diffracted from the sample S, and the gap H is the gap formed between the X-ray shielding member 20 and the sample S.

That is, a control program of the driving motor 30 may be set so that the X-ray shielding member 20 is moved to form the gap H on the basis of the above relational expression.

The present invention is not limited to the above embodiments, and various modifications may be made to the embodiments.

For example, the goniometer 10 is not limited to the construction shown in FIGS. 2 to 5, and the present invention may be applied to X-ray diffraction apparatuses in which various kinds of goniometers are mounted.

Furthermore, in the above embodiments, the X-ray shielding member is moved in only the direction perpendicular to the X-ray incident face of the sample, however, the X-ray shielding member may be moved in a direction parallel to the X-ray incident face of the sample. Still furthermore, the X-ray shielding member may be moved in conformity with the intersecting position (so-called cross-point) between the outer edge of the incident X-ray incident to the sample and the outer edge of the diffraction X-ray diffracted from the sample.

Furthermore, the X-ray diffraction apparatus of this invention is particularly effectively used in a case where it is impossible to dispose a receiving slit, an anti scatter slit or the like in front of the X-ray detector, such as when using a Time delay Integration (TDI)-CCD (one of readout systems of a CCD image sensor) which adds and synthesizes multiple CCD output signals, or when using a two-dimensional X-ray detector like a CCD or the like as the X-ray detector for detecting a diffraction X-ray linearly or in a planarly wide range. However, it is needless to say that the present invention can be applied to prevent traveling of scattered X-rays more surely even when the receiving slit or the anti scatter slit can be disposed in front of the X-ray detector.

The invention claimed is:

1. An X-ray diffraction apparatus having a configuration that a divergence angle of an X-ray emitted from an X-ray source is limited by a divergence angle limiting unit, the X-ray is irradiated to an X-ray incident face of a sample held on a sample table and a diffraction X-ray diffracted from the sample is detected by an X-ray detector, a configuration that positional relationship corresponding to relative angular relationship of the X-ray source, the X-ray incident face of the sample held on the sample table and the X-ray detector is changed by a goniometer to change an incident angle of the X-ray to the sample, and the X-ray detector is disposed so as to face a diffraction direction of the diffraction X-ray diffracted from the sample, and a configuration that an X-ray shielding member is provided so as to confront the X-ray incident face of the sample so that a gap through which an incident X-ray emitted from the X-ray source and irradiated to the X-ray incident face of the sample can pass, is formed between the X-ray shielding member and the X-ray incident face of the sample, comprising a gap adjusting unit that moves the X-ray shielding member in connection with the change of the X-ray incident angle to the sample by the goniometer during execution of the X-ray diffraction measurement, thereby adjusting the breadth of the gap formed between the X-ray shielding member and the X-ray incident face of the sample in conformity with the width of the incident X-ray to the sample or the full width of the diffraction X-ray diffracted from the sample.

2. The X-ray diffraction apparatus according to claim 1, wherein the gap adjusting unit comprises a guide support mechanism that is fixed to the sample table, and supports the X-ray shielding member to move and guide the X-ray shielding member in a direction perpendicular to the X-ray incident face of the sample, and a cam mechanism that moves the X-ray shielding member along the guide support mechanism.

3. The X-ray diffraction apparatus according to claim 2, wherein the goniometer has an X-ray incident angle adjusting mechanism that changes positional relationship corresponding to relative angular relationship between the X-ray incident face of the sample held on the sample table and the X-ray source to change the incident angle of the X-ray to the sample, and a detector swing arm that is swung around the X-ray incident face of the sample while the X-ray detector is mounted thereon, whereby positional relationship corresponding to relative angular relationship between the X-ray incident face of the sample held on the sample table and the X-ray detector is changed to dispose the X-ray detector in the diffraction direction of the diffraction X-ray diffracted from the sample, the cam mechanism has a cam fixed to the detector swing arm and a cam follower that is mounted on the X-ray shielding member and comes into contact with a cam face of the cam, and the cam face of the cam is shaped so as to move the X-ray shielding member in accordance with the change of the X-ray incident angle to the sample by the goniometer so that the breadth of the gap formed between the X-ray shielding member and the X-ray incident face of the sample is conformed with the width of the incident X-ray incident to the sample or the width of the diffraction X-ray diffracted from the sample.

4. The X-ray diffraction apparatus according to claim 1, wherein the gap adjusting unit has a guide support mechanism that is fixed to the sample table and guides the X-ray shielding member so that the X-ray shielding member is freely linearly movable so as to approach to and recede from the X-ray incident face of the sample, and a driving motor that drives the X-ray shielding member in accordance with the change of the X-ray incident angle to the sample by the goniometer so that the breadth of the gap formed between the X-ray shielding member and the X-ray incident face of the sample is conformed with the width of the incident X-ray incident to the sample or the width of the diffraction X-ray diffracted from the sample.

5. the X-ray diffraction apparatus according to claim 1, wherein the X-ray shielding member is a knife edge slit that is formed of a material through which X-rays never pass and designed in a plate-like shape having a sharp edge.

6. An X-ray diffraction apparatus, comprising:
   a divergence angle limiting unit limiting a divergence angle of an X-ray emitted from an X-ray source and irradiated to an X-ray incident face of a sample held on a sample table;
   an X-ray detector detecting a diffraction X-ray diffracted from the sample;
   an X-ray shielding member confronting the X-ray incident face of the sample so that a gap, through which an incident X-ray emitted from the X-ray source and irradiated to the X-ray incident face of the sample can pass, is formed between the X-ray shielding member and the X-ray incident face of the sample;
   a gap adjusting unit including a cam mechanism that moves the X-ray shielding member; and
   a goniometer including an X-ray incident angle adjusting mechanism that changes a positional relationship corresponding to a relative angular relationship between the X-ray incident face of the sample held on the sample table and the X-ray source to change the incident angle of the X-ray to the sample, and a detector swing arm that is swung around the X-ray incident face of the sample while the X-ray detector is mounted thereon, whereby the positional relationship corresponding to relative angular relationship between the X-ray incident face of the sample held on the sample table and the X-ray detector is changed to dispose the X-ray detector in the diffraction direction of the diffraction X-ray diffracted from the sample,
   wherein the cam mechanism has a cam fixed to the detector swing arm and a cam follower that is mounted on the X-ray shielding member and comes into contact with a cam face of the cam, and the cam face of the cam is shaped so as to move the X-ray shielding member in accordance with the change of the X-ray incident angle to the sample by the goniometer so that the breadth of the gap formed between the X-ray shielding member and the X-ray incident face of the sample is conformed with the width of the incident X-ray incident to the sample or the width of the diffraction X-ray diffracted from the sample.

* * * * *